(12) United States Patent
Stangeland et al.

(10) Patent No.: US 8,802,857 B2
(45) Date of Patent: Aug. 12, 2014

(54) PROCESS FOR PREPARING 4-[2-(2-FLUOROPHENOXYMETHYL) PHENYL]PIPERIDINE COMPOUNDS

(75) Inventors: Eric L. Stangeland, Pacifica, CA (US); Miroslav Rapta, San Carlos, CA (US)

(73) Assignee: Theravance Biopharma R&D IP, LLC, South San Francisco, CA (US)

(*) Notice: Subject to any disclaimer, the term of this patent is extended or adjusted under 35 U.S.C. 154(b) by 0 days.

(21) Appl. No.: 13/545,513

(22) Filed: Jul. 10, 2012

(65) Prior Publication Data
US 2012/0277438 A1 Nov. 1, 2012

Related U.S. Application Data

(62) Division of application No. 12/617,845, filed on Nov. 13, 2009, now Pat. No. 8,247,433.

(60) Provisional application No. 61/114,541, filed on Nov. 14, 2008.

(51) Int. Cl.
C07D 211/22 (2006.01)

(52) U.S. Cl.
USPC .......................................................... 546/236

(58) Field of Classification Search
USPC .......................................................... 546/236
See application file for complete search history.

(56) References Cited

U.S. PATENT DOCUMENTS

| | | | |
|---|---|---|---|
| 4,007,196 A | 2/1977 | Christensen et al. |
| 4,198,417 A | 4/1980 | Ong et al. |
| 4,229,449 A | 10/1980 | Melloni et al. |
| 4,243,807 A | 1/1981 | Friebe et al. |
| 5,023,269 A | 6/1991 | Robertson et al. |
| 5,037,841 A | 8/1991 | Schohe et al. |
| 5,614,518 A | 3/1997 | Leeson et al. |
| 6,518,284 B2 | 2/2003 | Orjales Venero et al. |
| 6,630,504 B2 | 10/2003 | Andrews et al. |
| 7,138,407 B2 | 11/2006 | Ruhland et al. |
| 7,294,637 B2 | 11/2007 | Aquila et al. |
| 7,378,436 B2 | 5/2008 | Fish et al. |
| 7,384,941 B2 | 6/2008 | Walter et al. |
| 7,888,386 B2 | 2/2011 | Stangeland et al. |
| 2005/0245519 A1 | 11/2005 | Barta et al. |
| 2006/0293360 A1 | 12/2006 | Bang-Andersen et al. |
| 2007/0072859 A1 | 3/2007 | Boulet et al. |
| 2007/0105870 A1 | 5/2007 | Bish et al. |
| 2007/0142389 A1 | 6/2007 | Bruendl et al. |
| 2009/0018132 A1 | 1/2009 | Degnan et al. |
| 2010/0125092 A1 | 5/2010 | Patterson et al. |
| 2010/0125093 A1 | 5/2010 | Patterson et al. |

FOREIGN PATENT DOCUMENTS

| | | |
|---|---|---|
| EP | 0 190 496 A2 | 8/1985 |
| WO | 00/20389 A2 | 4/2000 |
| WO | WO 2006/097766 A1 | 9/2006 |
| WO | 2007/072150 A2 | 6/2007 |
| WO | WO 2008/023258 A1 | 2/2008 |
| WO | WO2008039418 | * 4/2008 |
| WO | WO 2009/081259 A1 | 7/2009 |

OTHER PUBLICATIONS

Wikipedia "Tosyl" p. 1 (20120.*
Kamal et al. "Lipase-catalyzed . . . " Hel. Chem. Acta vo,90, p. 1723-1730 (2007).*
Blackburn "Teaching slides on textbook org. chem. by Wade" slide 1, 15 (2006).*
Gray et al. "Discovery and . . . " Bioorg. Med. Chem. 19 p. 6604-6607 (2009).*
Marcotullio et al. "A new simple . . . " Synthesis 16 p. 2760-2766 (2006).*
Ding et al. "Treatment of alcohols . . . " Molcules v. 16, 5665-5673 (2011).*
Bergel et al., "Synthetic Analgesics. Part I. Synthesis of Basic Benzofuran Derivatives and Certain 4-Phenylpiperidine Compounds", Journal of the Chemical Society, pp. 261-265 (1944).
Dounay et al., "Design, Synthesis, and Pharmacological Evaluation of Phenoxy Pyridyl Derivatives as Dual Norepinephrine Reuptake Inhibitors and 5-HT$_{1A}$ Partial Agonists", BioOrganic & Medicinal Chemistry Letters, pp. 1114-1117 (2010).
Gray et al., "Discovery and Pharmacological Characterization of Aryl Piperazine- and Piperidine Ethers as Dual Acting Norepinephrine Reuptake Inhibitors and 5-HT$_{1A}$ Partial Agonists", BioOrganic & Medicinal Chemistry Letters doi 10.1016/j.bmcl. 2009.10.014(2009).
Singer et al., "Synthesis and SAR of Tolylamine 5-HT$_6$ Antagonists", BioOrganic & Medicinal Chemistry Letters, pp. 2409-2412 (2009).
PCT Notification of Transmittal of the International Search Report and the Written Opinion of the International Searching Authority, or the Declaration of PCT/US2009/064304 dated Mar. 29, 2010.

* cited by examiner

*Primary Examiner* — Celia Chang
(74) *Attorney, Agent, or Firm* — Jeffrey A. Hagenah; Shelley Eberle

(57) ABSTRACT

The invention relates to processes and intermediates for preparing compounds of formula I:

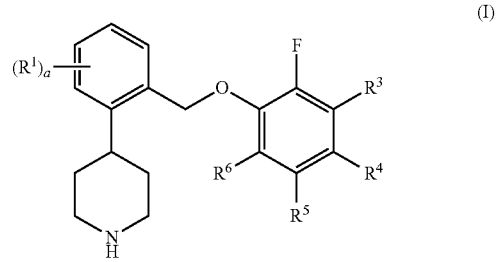

where a, $R^1$, and $R^{3-6}$ are as defined in the specification, or a salt thereof. The compounds of formula I are serotonin and norepinephrine reuptake inhibitors.

4 Claims, No Drawings

PROCESS FOR PREPARING 4-[2-(2-FLUOROPHENOXYMETHYL) PHENYL]PIPERIDINE COMPOUNDS

CROSS-REFERENCE TO RELATED APPLICATIONS

This application is a divisional application of U.S. Ser. No. 12/617,845, filed Nov. 13, 2009, now allowed, which claims the benefit of U.S. Provisional Application No. 61/114,541, filed on Nov. 14, 2008; the entire disclosures disclosure of which are is incorporated herein by reference in their entirety.

BACKGROUND OF THE INVENTION

1. Field of the Invention

The present invention relates to processes and intermediates for preparing 4-[2-(2-fluorophenoxymethyl)phenyl]piperidine compounds having activity as serotonin (5-HT) and norepinephrine (NE) reuptake inhibitors.

2. State of the Art

Pain is an unpleasant sensory and emotional experience associated with actual or potential tissue damage, or described in terms of such damage (International Association for the Study of Pain (IASP), Pain Terminology). Chronic pain persists beyond acute pain or beyond the expected time for an injury to heal (American Pain Society. "Pain Control in the Primary Care Setting." 2006:15). Neuropathic pain is pain initiated or caused by a primary lesion or dysfunction in the nervous system. Peripheral neuropathic pain occurs when the lesion or dysfunction affects the peripheral nervous system and central neuropathic pain when the lesion or dysfunction affects the central nervous system (IASP).

Several types of therapeutic agents are currently used to treat neuropathic pain including, for example, tricyclic antidepressants, serotonin and norepinephrine reuptake inhibitors, calcium channel ligands (e.g., gabapentin and pregabalin), topical lidocaine, and opioid agonists (e.g., morphine, oxycodone, methadone, levorphanol and tramadol).

The 4-[2-(2-fluorophenoxymethyl)phenyl]piperidine compounds described herein inhibit the reuptake of both serotonin and norepinephrine by binding to the serotonin and norepinephrine transporters. A need exists for an efficient process of preparing such compounds.

SUMMARY OF THE INVENTION

The present invention provides novel intermediates and processes for preparing compounds that have been found to possess serotonin reuptake inhibitory activity and norepinephrine reuptake inhibitory activity.

One aspect of the invention relates to a process for preparing a compound of formula I:

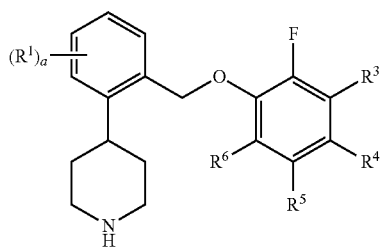

(I)

or a salt thereof, where: a is 0, 1, 2, 3, or 4; each $R^1$ is independently halo or trifluoromethyl; $R^3$ is hydrogen, halo, or —$C_{1-6}$alkyl; $R^4$, $R^5$, and $R^6$ are independently hydrogen or halo; the process comprising the steps of:

(a) reacting a compound of formula 1:

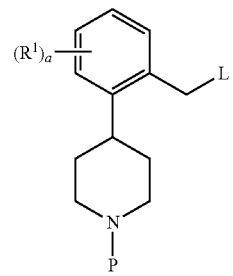

(1)

or a salt thereof, with a compound of formula 2:

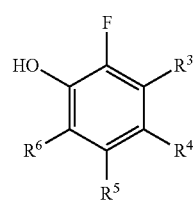

(2)

in the presence of a base, to provide a compound of formula 3:

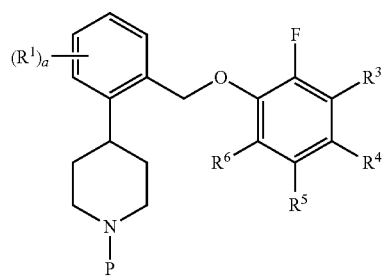

(3)

or a salt thereof, where L is a leaving group and P is an amino-protecting group; and (b) removing the amino-protecting group, P, from the compound of formula 3 or a salt thereof, to provide a compound of formula I or a salt thereof.

In one embodiment, the compound of formula I is 4-[2-(2,4,6-trifluorophenoxymethyl)phenyl]piperidine or a pharmaceutically acceptable salt thereof. In another embodiment, the compound of formula I is defined as:

(a) $R^3$ and $R^5$ are hydrogen and:
  (i) $R^4$ is fluoro, $R^6$ is fluoro, and a is 0;
  (ii) $R^4$ is fluoro, $R^6$ is fluoro, a is 1, and $R^1$ is 4-fluoro, 5-fluoro, 5-trifluoromethyl, or 6-fluoro;
  (iii) $R^4$ is fluoro, $R^6$ is fluoro, a is 2, and $R^1$ is 4,5-difluoro, 4,6-difluoro, or 5,6-difluoro;
  (iv) $R^4$ is fluoro, $R^6$ is chloro, and a is 0;
  (v) $R^4$ is chloro, $R^6$ is fluoro, and a is 0; or
  (vi) $R^4$ is bromo, $R^6$ is chloro, and a is 0; or (b) $R^3$ and $R^4$ are hydrogen, $R^5$ is fluoro, $R^6$ is chloro, and:
(i) a is 0;
(ii) a is 1 and $R^1$ is 5-fluoro or 6-fluoro; or
(iii) a is 2 and $R^1$ is 4,6-difluoro; or
(c) $R^4$ and $R^5$ are hydrogen, $R^6$ is fluoro and;
(i) $R^3$ is fluoro and a is 0;
(ii) $R^3$ is fluoro, a is 1, and $R^1$ is 3-fluoro, 5-fluoro, 5-trifluoromethyl, or 6-fluoro;
(iii) $R^3$ is fluoro, a is 2, and $R^1$ is 4,6-difluoro; or
(iv) $R^3$ is chloro or methyl, and a is 0; or
(d) $R^3$, $R^4$, and $R^5$ are hydrogen and:
(i) $R^6$ is H, and a is 0;
(ii) $R^6$ is H, a is 1, and $R^1$ is 5-fluoro or 6-fluoro;
(iii) $R^6$ is fluoro and a is 0;
(iv) $R^6$ is fluoro, a is 1, and $R^1$ is 4-fluoro, 5-fluoro, or 6-fluoro;
(v) $R^6$ is fluoro, a is 2, and $R^1$ is 4,5-difluoro or 4,6-difluoro;
(vi) $R^6$ is chloro and a is 0;
(vii) $R^6$ is chloro, a is 1, and $R^1$ is 4-fluoro, 6-fluoro, or 5-trifluoromethyl;
(viii) $R^6$ is chloro, a is 2, and $R^1$ is 4,5-difluoro; or
(ix) $R^6$ is bromo and a is 0;
or a pharmaceutically acceptable salt thereof.

Another aspect of the invention relates to a process for preparing a compound of formula 1 or a salt thereof, the process comprising the steps of:
(a') reacting a compound of formula 4:

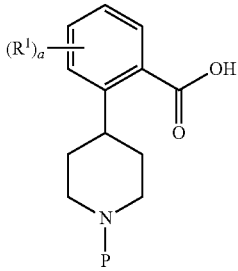

(4)

or a salt thereof, with a reducing agent to provide a compound of formula 5:

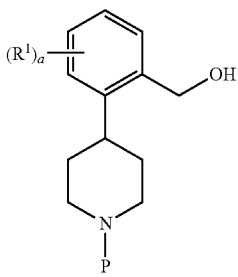

(5)

or a salt thereof; and
(b') converting the hydroxyl group of the compound of formula 5 or a salt thereof, into a leaving group, L, to provide a compound of formula 1 or a salt thereof.

Still another aspect of the invention relates to a novel intermediates used in the processes of the invention. In one such aspect of the invention novel intermediates have formula 1:

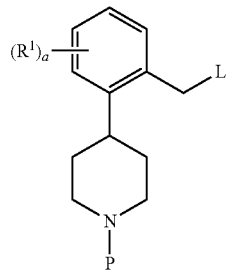

(1)

or a salt thereof, where: L is bromo, iodo, or —OS(O$_2$)—R, where R is —C$_{1-4}$alkyl or phenyl, and the phenyl is optionally substituted with —C$_{1-4}$alkyl, halo or nitro; a is 0, 1, 2, 3, or 4; each $R^1$ is independently halo or trifluoromethyl; and P is an amino-protecting group.

DETAILED DESCRIPTION OF THE INVENTION

The invention relates to novel processes for preparing compounds of formula I:

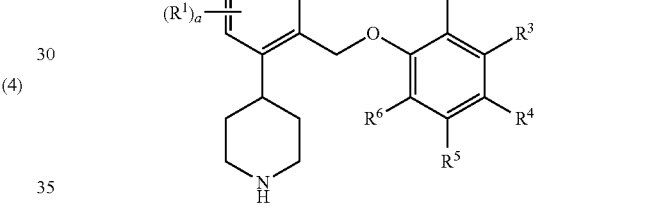

(I)

and compounds of formula 1:

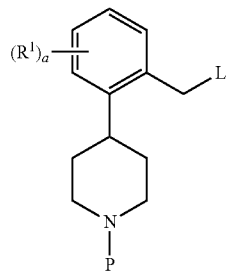

(1)

or a salt thereof.

The integer "a" is 0, 1, 2, 3, or 4. In one particular embodiment, a is 0 (i.e., $R^1$ is absent), 1, or 2. Each $R^1$ moiety is independently halo or trifluoromethyl. The $R^3$ moiety is hydrogen, halo, or —C$_{1-6}$alkyl. Each $R^4$, $R^5$, and $R^6$ moiety is independently hydrogen or halo. In one particular embodiment, a is 0. In another embodiment, a is 0, $R^3$ and $R^5$ are hydrogen, and $R^4$ and $R^6$ are fluoro.

DEFINITIONS

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The compounds described herein have typically been named using the AutoNom feature of the commercially-available MDL® ISIS/Draw software (Symyx, Santa Clara, Calif.). Typically, compounds of formula I have been named as 4-[2-(2-fluorophenoxymethyl)phenyl]piperidines. Numbering of the compounds described herein is as follows:

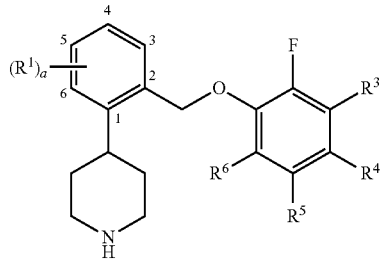

As used herein, the phrase "having the formula" or "having the structure" is not intended to be limiting and is used in the same way that the term "comprising" is commonly used.

The term "alkyl" means a monovalent saturated hydrocarbon group which may be linear or branched. Unless otherwise defined, such alkyl groups typically contain from 1 to 10 carbon atoms and include, for example, —$C_{1-2}$alkyl, —$C_{1-3}$alkyl, —$C_{1-4}$alkyl, —$C_{1-6}$alkyl, and —$C_{1-8}$alkyl. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl, and the like.

When a specific number of carbon atoms is intended for a particular term used herein, the number of carbon atoms is shown preceding the term as subscript. For example, the term "—$C_{1-6}$alkyl" means an alkyl group having from 1 to 6 carbon atoms, where the carbon atoms are in any acceptable configuration.

The term "halo" means fluoro, chloro, bromo and iodo.

As used herein, the phrase "of the formula", "having the formula" or "having the structure" is not intended to be limiting and is used in the same way that the term "comprising" is commonly used.

The term "salt" when used in conjunction with a compound means a salt of the compound derived from an inorganic or organic base or from an inorganic or organic acid. In addition, when a compound of formula I contains both a basic moiety, such as an amine, and an acidic moiety such as a carboxylic acid, zwitterions may be formed and are included within the term "salt" as used herein. Salts derived from inorganic bases include aluminum, ammonium, calcium, copper, ferric, ferrous, lithium, magnesium, manganic, manganous, potassium, sodium, zinc, and the like. Particularly preferred are ammonium, calcium, magnesium, potassium and sodium salts. Salts derived from organic bases include salts of primary, secondary and tertiary amines, including substituted amines, cyclic amines, naturally-occurring amines, and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine, and the like. Salts derived from inorganic acids include salts of boric, carbonic, hydrohalic (hydrobromic, hydrochloric, hydrofluoric or hydroiodic), nitric, phosphoric, sulfamic and sulfuric acids. Salts derived from organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. Particularly preferred are citric, hydrobromic, hydrochloric, maleic, phosphoric, sulfuric and tartaric acids. The term "pharmaceutically acceptable salt" means a salt prepared from a base or an acid which is acceptable for administration to a patient, such as a mammal (e.g., salts having acceptable mammalian safety for a given dosage regime). However, it is understood that the salts covered by the invention are not required to be pharmaceutically acceptable salts, such as salts of intermediate compounds that are not intended for administration to a patient.

All other terms used herein are intended to have their ordinary meaning as understood by those of ordinary skill in the art to which they pertain.

Process Conditions

Suitable inert diluents for use in the process of the invention include, by way of illustration and not limitation, organic diluents such as acetic acid, tetrahydrofuran (THF), acetonitrile (MeCN), N,N-dimethylformamide (DMF), N,N-dimethylacetamide, N-methylpyrrolidinone, dimethyl sulfoxide (DMSO), toluene, dichloromethane (DCM), acetone, ethyl acetate, isopropyl acetate, methyl t-butyl ether, chloroform (CHCl$_3$), carbon tetrachloride (CCl$_4$), 1,4-dioxane, methanol, ethanol, propanol, isopropanol, butanol, ethylene glycol, and the like. Aqueous diluents may also be used, and include water as well as basic and acidic aqueous diluents. Combinations of any of the foregoing diluents are also contemplated.

There are numerous bases that are suitable for use in the process of the invention. Exemplary organic bases include, by way of illustration and not limitation: amines including primary alkylamines (e.g., methylamine, ethanolamine, the buffering agent tris, and the like), secondary alkylamines (e.g., dimethylamine, methylethanolamine, N,N-diisopropylethylamine (DIPEA), and the like), tertiary amines (e.g., trimethylamine, triethylamine, triethylenediamine, and the like); ammonia compounds such as ammonium hydroxide and hydrazine; alkali metal hydroxides such as sodium hydroxide, sodium methoxide, potassium hydroxide, potassium t-butoxide, and the like; metal hydrides; and alkali metal carboxylate salts such as sodium acetate and the like). Exemplary inorganic bases, include, by way of illustration and not limitation: alkali metal carbonates such as lithium carbonate, potassium carbonate, cesium carbonate, sodium carbonate, sodium bicarbonate, and the like; other carbonates such as calcium carbonate and the like; and alkali metal phosphates such as potassium phosphate and the like).

All reactions are typically conducted at a temperature within the range of about −78° C. to about 110° C., for example at room temperature. Reactions may be monitored by use of thin layer chromatography (TLC), high performance liquid chromatography (HPLC), and/or LCMS until completion. Reactions may be complete in minutes, may take hours, typically from 1-2 hours and up to 48 hours, or days, such as up to 3-4 days.

Upon completion of any of the process steps, the resulting mixture or reaction product may be further treated in order to obtain the desired product. For example, the resulting mixture or reaction product may be subjected to one or more of the following procedures: dilution (for example with saturated $NaHCO_3$ or EtOAc); extraction (for example, with EtOAc, $CHCl_3$, DCM, aqueous HCl); washing (for example, with DCM, 1.0 M NaOH in water, saturated aqueous NaCl, or saturated $NaHCO_3$); distillation; drying (for example, over $MgSO_4$ or $Na_2SO_4$, or in vacuo); precipitation; filtration; being redissolved (for example in a 1:1 acetic acid:$H_2O$ solution); purification (for example by preparative HPLC, reverse phase preparative HPLC, or crystallization); and/or crystallizing (for example, from EtOAc/ethanol or isopropanol/water); and/or being concentrated (for example, in vacuo).

The process for preparing a compound of formula I or a salt thereof is conducted in two steps. The first step of the process is a nucleophilic displacement coupling reaction, which involves combining the compound of formula 1 or a salt thereof with a 2-fluorophenol compound of formula 2 in the presence of a base to form a compound of formula 3 or a salt thereof.

The compound of formula 1 and salts thereof can be prepared by techniques that are known in the art of by the methods described herein. The 2-fluorophenol compound is either commercially available, or is readily synthesized by techniques that are well known in the art.

In one embodiment, a slight excess of the 2-fluorophenol compound is used based on the amount of the compound of formula 1. In one embodiment, from about 1.0 to about 2.0 equivalents of the 2-fluorophenol compound are used, and in another embodiment, about 1.0 to 1.5 equivalents are used.

Typically, the compound of formula 1 is dissolved in an inert diluent, then added to the 2-fluorophenol compound and a base. In one embodiment, an excess of base is used based on the amount of the compound of formula 1. In one embodiment, from about 2.0 to about 4.0 equivalents of the base are used, and in another embodiment, about 3.0 equivalents are used. In one embodiment, the base is an alkali metal carbonate, and in one particular embodiment, potassium carbonate. Exemplary inert diluents include acetonitrile.

Formation of the compound of formula 3 or a salt thereof is typically conducted at a temperature ranging from about 40° C. to about 60° C.; and in one embodiment at a temperature ranging from about 45° C. to about 55° C. for about 5 to about 24 hours. The reaction mixture is then allowed to cool to room temperature.

When formation of compound of formula 3 or a salt thereof is substantially complete, the supernatant can be separated from the base and other solids and used in the next step. Alternately, the resulting product can be isolated and purified by conventional procedures prior to the deprotection step.

The compound of formula 1 has a leaving group, which is depicted as "L", which is a functional group or atom which can be displaced by another functional group or atom in a substitution reaction, such as a nucleophilic substitution reaction. By way of example, representative leaving groups include halogens (e.g., chloro, bromo and iodo groups); sulfonic ester groups, such as mesylate, tosylate, brosylate, nosylate and the like; and acyloxy groups, such as acetoxy, trifluoroacetoxy and the like. Of particular interest are sulfonic ester groups, which can be depicted by the formula —$OS(O_2)$—R, where R is —$C_{1-4}$alkyl or phenyl, and the phenyl group may be substituted with —$C_{1-4}$alkyl, halo or nitro. In one particular embodiment, the leaving group is —$OS(O_2)$—$CH_3$ or —$OS(O_2)$—4-methylphenyl.

The compounds of formula 1 and formula 3 have an amino-protecting group, which is depicted as "P", which is a group covalently attached to the amino functional group that prevents the functional group from undergoing undesired reactions but which permits the functional group to be regenerated (i.e., deprotected or unblocked) upon treatment of the protecting group with a suitable reagent. Representative amino-protecting groups include, but are not limited to, t-butoxycarbonyl (Boc), trityl (Tr), benzyloxycarbonyl (Cbz), 9-fluorenylmethoxycarbonyl (Fmoc), formyl, trimethylsilyl (TMS), t-butyldimethylsilyl (TBS), and the like. In one particular embodiment, the amino-protecting group is Boc. Other representative amino protecting groups are described, for example, in T. W. Greene and G. M. Wuts, *Protecting Groups in Organic Synthesis*, Third Edition, Wiley, New York, 1999.

The second step of the process is a deprotection step, which involves removing the amino-protecting group, P, from the compound of formula 3 or a salt thereof, to provide a compound of formula I or a salt thereof. Standard deprotection techniques and reagents such as TFA (alone or in DCM) or HCl (in 1,4-dioxane or ethanol) are used to remove the P group. For example, a Boc group can be removed using an acidic reagent such as hydrochloric acid, trifluoroacetic acid, and the like; while a Cbz group can be removed by employing catalytic hydrogenation conditions such as $H_2$ (1 atm), 10% Pd/C in an alcoholic solvent.

Typically, the compound of formula 3 and the deprotecting reagent are combined, optionally in an inert diluent. An excess amount of reagent is used. In one embodiment from about 5.0 to about 25.0 equivalents of the reagent are used based on the amount of the compound of formula 3; and in another embodiment from about 10.0 to about 20.0 equivalents of the reagent are used.

This deprotection step is typically conducted at a temperature ranging from about 10° C. to about 30° C.; and in one embodiment at a temperature ranging from about 15° C. to about 25° C. for about 20 to about 28 hours, and in one embodiment for about 24 hours or overnight, or until the reaction is substantially complete. In one embodiment, the deprotecting reagent is TFA or HCl in EtOH.

When formation of compound of formula I or a salt thereof is substantially complete, the resulting product can then be isolated and purified by conventional procedures. The compound of formula I may be crystallized by further treatment with ethyl acetate and ethanol, and optionally recrystallized with isopropanol and water.

The process for preparing a compound of formula 1 or a salt thereof is conducted in two steps. The first step of the process is a borane reduction reaction, which involves combining one equivalent of a compound of formula 4 or a salt thereof with one or more equivalents of a reducing agent to form a compound of formula 5 or a salt thereof.

Typically, the reducing agent is slowly added to a mixture of the compound of formula 4 in an inert diluent such as tetrahydrofuran. In one embodiment, about 1.5 to 2.5 equivalents of the reducing agent are used based on the amount of compound of formula 4; and in another embodiment, about 2.0 equivalents are used.

The compound of formula 4, for example, 4-(2-carboxyphenyl)piperidine-1-carboxylic acid t-butyl ester (P=Boc), is commercially available. Suitable reducing agents include borane dimethyl sulfide complex, 9-borabicyclo[3.3.1]nonane, borane 1,2-bis(t-butylthio)ethane complex, borane t-butylamine complex, borane di(t-butyl)phosphine complex, borane-tetrahydrofuran complex and so forth. In one particular embodiment, the reducing agent is borane dimethyl sulfide complex or borane-tetrahydrofuran complex.

Formation of the compound of formula 5 is typically conducted at a temperature ranging from about 20° C. to about 70° C.; and in one embodiment is briefly stirred at room temperature, then heated to about 40° C. to 60° C., for a time period ranging from 40 to 120 minutes, and in one embodiment, 60 minutes, or until formation of the compound of formula 5 is substantially complete. The reaction is typically conducted under nitrogen. When formation of the compound of formula 5 is substantially complete, the reaction may be quenched, and the resulting product is then isolated and purified by conventional procedures.

The second step of the process involves converting the hydroxyl group of the compound of formula 5 or a salt thereof, into a leaving group, L, to provide a compound of formula 1 or a salt thereof.

Typically one equivalent of a compound of formula 5 is combined with one or more equivalents of a reagent suitable for converting the hydroxyl group to a leaving group. In one embodiment, about 1.0 to 1.7 equivalents of the reagent are used based on the amount of compound of formula 5; and in another embodiment, about 1.1 to about 1.5 equivalents are used.

Formation of the formula 1 or a salt thereof is typically conducted at a temperature ranging from about −10° C. to about 10° C.; and in at about 0° C., for a time period ranging from 40 to 120 minutes, and in one embodiment, from 60 to 90 minutes, or until formation of the compound of formula 1 or a salt thereof is substantially complete. The reaction is typically conducted under nitrogen. When formation of the compound of formula 1 or a salt thereof is substantially complete, the resulting product is then isolated and/or purified by conventional procedures.

Suitable reagents for converting the hydroxyl group to a halogen leaving group include halogenating agents such as: thionyl chloride or phosphorus trichloride (where L=Cl); carbon tetrabromide (with triphenylphosphine or potassium carbonate), hydrogen bromide, or phosphorus tribromide (where L=Br); cesium iodine (with aluminum trichloride (((where L=I); and so forth.

Suitable reagents for converting the hydroxyl group to a sulfonic ester group leaving group include p-toluenesulfonyl chloride (forming a tosylate where L=—OS(O$_2$)-4-methylphenyl), methanesulfonic anhydride (forming a mesylate where L=—OS(O$_2$)—CH$_3$), p-bromobenzenesulfonyl chloride (forming a brosylate where L=—OC(O)-4-bromophenyl), p-nitrobenzenesulfonyl chloride (forming a nosylate where L=—OC(O)-4-nitrophenyl), and so forth. This reaction is typically conducted in a suitable base. In one embodiment, about 1.2 to 1.8 equivalents of the base are used based on the amount of compound of formula 5; and in another embodiment, about 1.4 to 1.6 equivalents are used. Exemplary bases for use with such reagents include secondary alkylamines such as N,N-diisopropylethylamine and tertiary amines such as triethylenediamine.

Suitable reagents for converting the hydroxyl group to an acyloxy group leaving group include acetyl chloride (where L=acetoxy or —OC(O)CH$_3$), trifluoroacetyl chloride (where L=trifluoroacetoxy —OC(O)CF$_3$), and so forth. Such reagents are typically used with an inert diluent such as tetrahydrofuran.

In one embodiment the reagent for converting the hydroxyl group is p-toluenesulfonyl chloride or methanesulfonic anhydride. Additional details of this reaction are described, for example, in Hartung et al. (1997) *Synthesis* 12:1433-1438.

Certain of the intermediates described herein are believed to be novel and accordingly, such compounds are provided as further aspects of the invention including, for example, of formula 1:

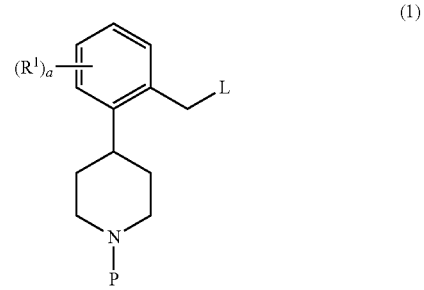

(1)

or a salt thereof, where: L is bromo, iodo, or —OS(O$_2$)—R, where R is —C$_{1-4}$alkyl or phenyl, and the phenyl is optionally substituted with —C$_{1-4}$alkyl, halo or nitro; a is 0, 1, 2, 3, or 4; each R$^1$ is independently halo or trifluoromethyl; and P is an amino-protecting group. In one particular embodiment, L is —OS(O$_2$)—R and R is methyl or 4-methyl-phenyl; a is 0; and P is t-butoxycarbonyl.

Further details regarding specific reaction conditions and other procedures for preparing representative compounds of the invention or intermediates thereof are described in the Examples set forth below.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard meaning:

AcOH acetic acid
Boc t-butoxycarbonyl
DCM dichloromethane (i.e., methylene chloride)
DIPEA N,N-diisopropylethylamine
EtOAc ethyl acetate
EtOH ethanol
IPA isopropyl alcohol
IPAc isopropyl acetate MeCN acetonitrile (CH₃CN)
McOH methanol
TFA trifluoroacetic acid
THF tetrahydrofuran
TsCl p-toluenesulfonyl chloride or 4-methylbenzenesulfonyl chloride Any other abbreviations used herein but not defined have their standard, generally accepted meaning. Unless noted otherwise, all materials, such as reagents, starting materials and solvents, were purchased from commercial suppliers (such as Sigma-Aldrich, Fluka Riedel-de Haën, and the like) and were used without further purification.

Preparation 1

4-[2-(Toluene-4-sulfonyloxymethyl)phenyl]piperidine-1-carboxylic Acid t-Butyl Ester

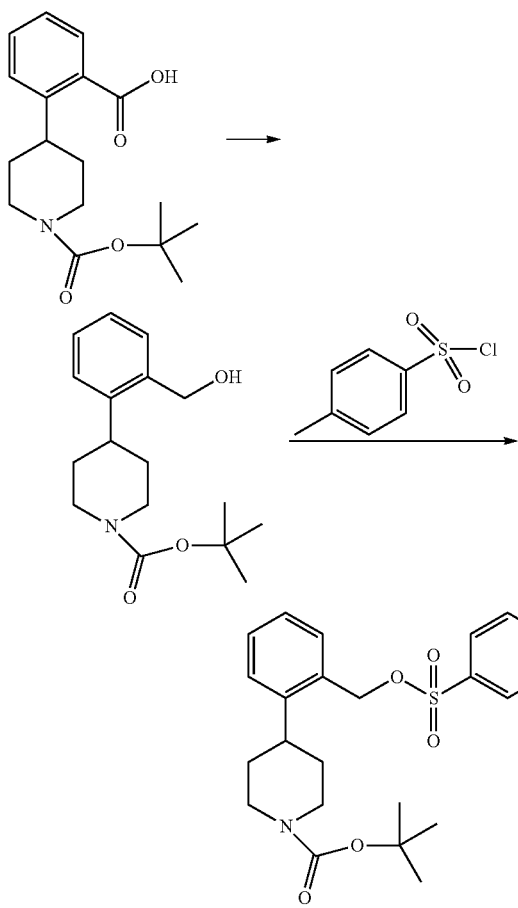

4-(2-Carboxyphenyl)piperidine-1-carboxylic acid t-butyl ester (5.0 g, 16 mmol, 1.0 eq.) and THF (130 mL, 1.7 mol) were combined at room temperature under nitrogen. Borane dimethyl sulfide complex (2.9 mL, 33 mmol, 2.0 eq.) was added dropwise and the mixture was stirred for 5 minutes, then heated at reflux for 1 hour. The mixture was cooled to room temperature, and the reaction was quenched dropwise with MeOH (40 mL), then concentrated by rotary evaporation. The material was azeotroped with MeOH (2×40 mL). The mixture was then diluted with EtOAc (100 mL), and washed with 1 M HCl (2×50 mL), then NaHCO₃ (2×50 mL), then saturated aqueous NaCl (1×50 mL). The organic layer was dried over anhydrous Na₂SO₄, filtered, and concentrated in vacuo to yield 4-(2-hydroxymethylphenyl)piperidine-1-carboxylic acid t-butyl ester (4.8 g) as a clear, light yellow oil that solidified upon sitting.

¹H NMR (CDCl₃) δ (ppm) 7.34-7.22 (m, 3H); 7.19 (dt, J=1.6 Hz, 7.2, 1H); 4.73 (s, 2H); 4.32-4.14 (m, 2H); 3.00 (tt, J=4.0 Hz, 12.0, 1H); 2.80 (t, J=11.6 Hz, 2H); 1.78-1.56 (m, 4H); 1.47 (m, 9H).

4-(2-Hydroxymethylphenyl)piperidine-1-carboxylic acid t-butyl ester (0.4 g, 1.0 mmol, 1.0 eq.) and triethylenediamine (220 mg, 2.0 mmol, 1.4 eq.) were dissolved in DCM (11 mL, 170 mmol). The mixture was cooled at 0° C. under nitrogen, TsCl (290 mg, 1.5 mmol, 1.1 eq.) was added, and the mixture was stirred at 0° C. for an additional 60 minutes. The mixture was diluted with EtOAc (50 mL) and washed with water (2×25 mL). The organic layer was dried over anhydrous Na₂SO₄, filtered and concentrated by rotary evaporation to yield the title compound (500 mg), which was used without further purification.

¹H NMR (CDCl₃) δ (ppm) 7.81 (t, J=2.0 Hz, 1H); 7.79 (t, J=2.0 Hz, 1H); 7.37-7.32 (m, 4H); 7.25-7.21 (m, 1H); 7.21-7.13 (m, 1H); 5.12 (s, 2H); 4.34-4.12 (m, 2H); 2.81-2.61 (m, 3H); 2.45 (s, 3H); 1.70-1.52 (m, 4H); 1.48 (s, 9H).

Preparation 2

4-(2-Methanesulfonyloxymethylphenyl)piperidine-1-carboxylic Acid t-Butyl Ester

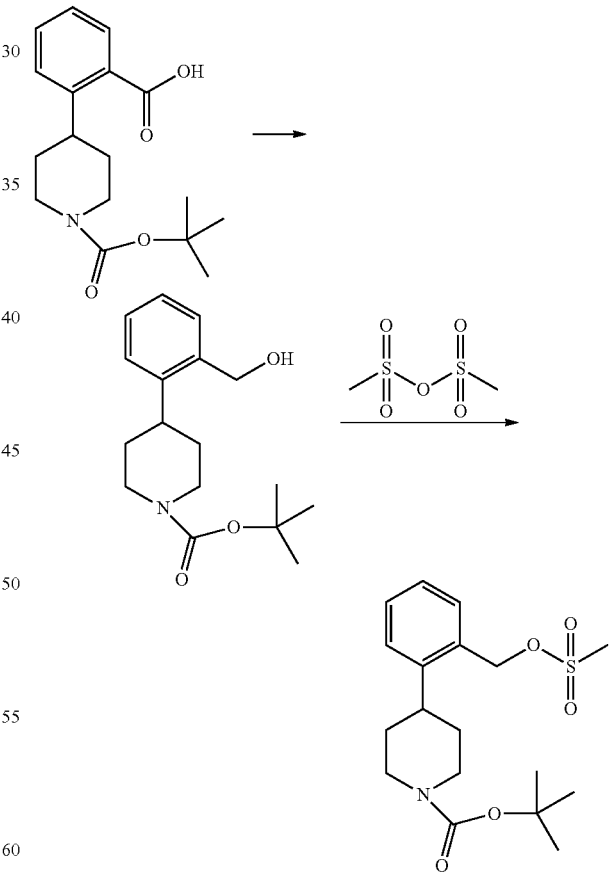

4-(2-Carboxyphenyl)piperidine-1-carboxylic acid t-butyl ester (5.0 g, 160 mmol, 1.0 eq.) and THF (100 mL, 1.0 mol) were combined at room temperature under nitrogen. 1.0M Borane-THF complex in THF (32.7 mL, 32.7 mmol, 2.0 eq.) was added dropwise over 10 minutes (5° C. exotherm, gas evolution). The mixture was stirred at room temperature for 5 minutes, then heated at 50° C. for 1 hour. The mixture was cooled to room temperature, and the reaction was quenched slowly with MeOH (30 mL) (mild exotherm, significant gas evolution), then concentrated by rotary evaporation. The material was azeotroped with MeOH (2×50 mL). The crude product was dissolved in EtOAc (100 mL, 1 mol), washed with NaHCO$_3$ (50 mL), then saturated aqueous NaCl (50 mL). The organic layer was dried over anhydrous Na$_2$SO$_4$, filtered, and concentrated in vacuo to yield 4-(2-hydroxymethylphenyl)piperidine-1-carboxylic acid t-butyl ester (4.4 g) as a clear, light yellow oil that solidified upon sitting.

4-(2-Hydroxymethylphenyl)piperidine-1-carboxylic acid t-butyl ester (50.0 g, 172 mmol, 1.0 eq.) was dissolved in DCM (500 mL, 8000 mmol). The mixture was cooled at 0° C. under nitrogen and methanesulfonic anhydride (44.8 g, 257 mmol, 1.5 eq.) was added in one portion. DIPEA (47.8 mL, 274 mmol, 1.6 eq.) was added dropwise over 5 minutes and the mixture was stirred at 0° C. for 90 minutes. Water (400 mL, 20 mol) was added and the mixture was stirred for 5 minutes. The phases were separated, and the organic layer was washed with water (300 mL), dried over Na$_2$SO$_4$, and the solvent removed to yield the title compound (70 g) as a thick oil, which was used without further purification.

$^1$H NMR (400 MHz, DMSO-d$_6$) δ (ppm) 7.37-7.43 (m, 3H), 7.31 (d, 1H), 7.22 (m, 2H), 5.38 (s, 2H), 4.28 (m, 2H), 2.92-3.10 (m, 1H), 2.92 (s, 3H), 2.80-2.92 (m, 2H), 1.63-1.81 (m, 4H), 1.51 (s, 9H).

Example 1

4-[2-(2,4,6-Trifluorophenoxymethyl)phenyl]piperidine

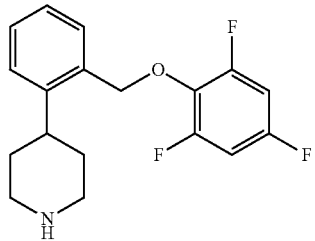 [SMILES: Fc1cc(F)c(OCc2ccccc2C2CCNCC2)c(F)c1]

4-[2-(Toluene-4-sulfonyloxymethyl)phenyl]piperidine-1-carboxylic acid t-butyl ester (2.1 g, 4.7 mmol, 1.0 eq.) was dissolved in MeCN (46 mL, 890 mmol) and added to K$_2$CO$_3$ (1.9 g, 14 mmol, 3.0 eq.) and 2,4,6-trifluorophenol (1.0 g, 7.0 mmol, 1.5 eq.). The mixture was shaken at 50° C. overnight, then cooled to room temperature. The supernatant was separated from the K$_2$CO$_3$ and other solids. TFA (7 mL, 90 mmol, 20.0 eq.) was added to the supernatant and the mixture was shaken overnight at room temperature. The solution was then concentrated to yield a crude residue. The residue was dissolved in 5.0 mL 1:1 AcOH/H$_2$O, then in an additional 2.0 mL AcOH, filtered and purified by preparative HPLC to yield the title compound as a TFA salt (1.3 g, 97.5% purity). MS m/z: [M+H]$^+$ calcd for C$_{18}$H$_{18}$F$_3$NO, 322.13. found 322.2.

$^1$H NMR (CDCl$_3$) δ (ppm) 9.83 (br.s, 1H); 9.32 (br.s, 1H); 7.46-7.39 (m, 2H); 7.32 (d, J=6.8 Hz, 1H); 7.26-7.21 (m, 1H); 6.76-6.66 (m, 2H); 5.07 (s, 2H); 3.69-3.50 (m, 2H); 3.38 (t, J=11.6 Hz, 1H); 3.20-3.02 (m, 2H); 2.19 (q, J=12.8 Hz, 2H); 2.12-2.01 (m, 2H).

Synthesis of 4-[2-(2,4,6-Trifluorophenoxymethyl) phenyl]piperidine as a HCl Salt 4-(2-Methanesulfonyloxymethylphenyl)piperidine-1-carboxylic acid t-butyl ester (27.0 g, 60.6 mmol, 1.0 eq.) was dissolved in McCN (540 mL) and added to K$_2$CO$_3$ (25 g, 180 mmol, 3.0 eq.) and 2,4,6-trifluorophenol (13.5 g, 90.9 mmol, 1.5 eq.). The mixture was vigorously stirred at 50° C. for 6 hours, removed from the heat, and stirred overnight. The mixture was cooled at room temperature, and diluted with EtOAc (700 mL) and water (700 mL). The phases were separated, and the organic layer was washed twice with 1.0 M NaOH in water (2×400 mL) and saturated aqueous NaCl (1×400 mL), then dried over Na$_2$SO$_4$ and the solvent removed to yield crude 4-[2-(2,4,6-trifluorophenoxymethyl)-phenyl]piperidine-1-carboxylic acid t-butyl ester (25.0 g). The crude product was combined with smaller scale runs for a total of 30 g, and purified by chromatography (0-10% EtOAc in hexanes) to yield 442-(2,4,6-trifluorophenoxymethyl)phenylpiperidine-1-carboxylic acid t-butyl ester (22.0 g).

The t-butyl ester (22.0 g, 31.3 mmol, 1.0 eq.) was combined with 1.25M HCl in EtOH (250 mL, 310 mmol, 10.0 eq.). The mixture was stirred at room temperature for 8 hours, then stored at −10° C. over approximately 48 hours. Most of solvent was removed by rotary evaporation. To the resulting thick slurry was added EtOAc (80 mL), followed by stirring at room temperature for 2 hours. First crop was isolated by filtration, and the filter cake was washed with EtOAc (20 mL) and dried to yield the title compound as a hydrochloride salt (8.5 g, >99% purity) white solid. HPLC of the filtrate shows ~25% area of product. For the second crop, the solvent was removed by rotary evaporation and the resulting solid (~10 g) was slurried in EtOAc (40 mL), first at room temperature, then at 60° C., and again at room temperature to yield the title compound as a hydrochloride salt (1.7 g, >99% purity).

Example 2

4-[2-(2,6-Difluorophenoxymethyl)phenyl]piperidine

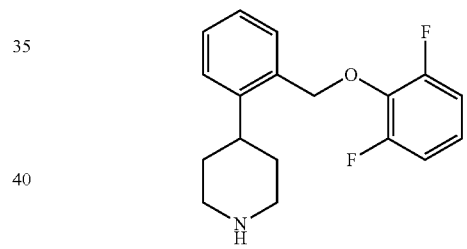

4-[2-(Toluene-4-sulfonyloxymethyl)phenyl]piperidine-1-carboxylic acid t-butyl ester (225 mg, 505 µmol, 1.0 eq.) was dissolved in MeCN (5.0 mL, 97 mmol) and added to K$_2$CO$_3$ (210 mg, 1.5 mmol, 3.0 eq.) and 2,6-difluorophenol (98 mg, 760 µmol, 1.5 eq.). The mixture was shaken at 50° C. overnight, then cooled to room temperature. The supernatant was separated from the K$_2$CO$_3$ and other solids.

TFA (800 µL, 10 mmol, 20.0 eq.) was added to the supernatant and the mixture was shaken overnight at room temperature. The solution was then concentrated to yield a crude residue. The residue was dissolved in 1.5 mL 1:1 AcOH/H$_2$O, then in an additional 0.3 mL AcOH, filtered and purified by preparative HPLC to yield the title compound as a TFA salt (115 mg, 95% purity). MS m/z: [M+H]$^+$ calcd for C$_{18}$H$_{19}$F$_2$NO, 304.14. found 304.2.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

The invention claimed is:

1. A process for preparing a compound of formula 1:

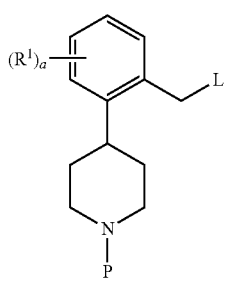
(1)

or a salt thereof, where L is a sulfonic ester group having the formula —OS(O$_2$)—R, where R is —C$_{1-4}$-alkyl or phenyl, and the phenyl group is optionally substituted with —C$_{1-4}$-alkyl, halo or nitro; and P is an amino-protecting group; the process comprising the steps of:

(a') reacting a compound of formula 4:

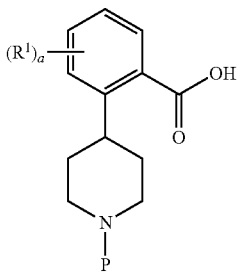
(4)

or a salt thereof, with a reducing agent to provide a compound of formula 5:

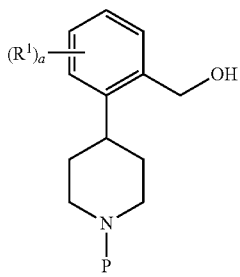
(5)

or a salt thereof; and (b') converting the hydroxyl group of the compound of formula 5 or a salt thereof, into a sulfonic ester group, L, to provide a compound of formula 1 or a salt thereof.

2. The process of claim 1, where L is —OS(O$_2$)—CH$_3$ or —OS(O$_2$)-4-methylphenyl.

3. The process of claim 1, where the reducing agent is borane dimethyl sulfide complex or borane-tetrahydrofuran complex.

4. The process of claim 1, where p-toluenesulfonyl chloride or methanesulfonic anhydride is used in step (b').

* * * * *

UNITED STATES PATENT AND TRADEMARK OFFICE
CERTIFICATE OF CORRECTION

PATENT NO. : 8,802,857 B2
APPLICATION NO. : 13/545513
DATED : August 12, 2014
INVENTOR(S) : Eric L. Stangeland et al.

Page 1 of 1

It is certified that error appears in the above-identified patent and that said Letters Patent is hereby corrected as shown below:

In the Claims

At Column 15, lines 1-15, Claim 1, the structure should be

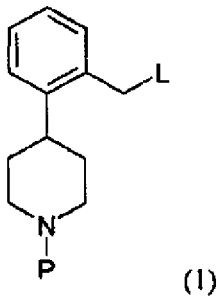

(1)

At Column 15, lines 21-32, Claim 1, the structure should be

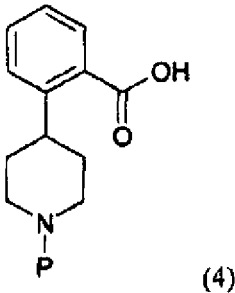

(4)

At Column 16, lines 5-15, Claim 1, the structure should be

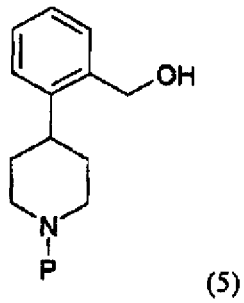

(5)

Signed and Sealed this
Thirty-first Day of March, 2015

Michelle K. Lee
*Director of the United States Patent and Trademark Office*